United States Patent
Strebelle et al.

(10) Patent No.: US 7,943,099 B2
(45) Date of Patent: May 17, 2011

(54) REACTOR AND METHOD FOR REACTING AT LEAST TWO GASES IN THE PRESENCE OF A LIQUID PHASE

(75) Inventors: Michel Strebelle, Brussels (BE); Michel Lempereur, Corbais (BE)

(73) Assignee: SOLVAY (Societe Anonyme), Brussels (BE)

( * ) Notice: Subject to any disclaimer, the term of this patent is extended or adjusted under 35 U.S.C. 154(b) by 570 days.

(21) Appl. No.: 11/719,652

(22) PCT Filed: Nov. 18, 2005

(86) PCT No.: PCT/EP2005/056055
§ 371 (c)(1),
(2), (4) Date: Oct. 30, 2007

(87) PCT Pub. No.: WO2006/053895
PCT Pub. Date: May 26, 2006

(65) Prior Publication Data
US 2009/0187052 A1     Jul. 23, 2009

(30) Foreign Application Priority Data

Nov. 19, 2004  (FR) ..................... 04 12311

(51) Int. Cl.
*B01J 19/26*     (2006.01)
*C07C 17/02*     (2006.01)
*C07C 17/04*     (2006.01)
(52) U.S. Cl. ......... 422/234; 422/140; 422/231; 570/246
(58) Field of Classification Search ............ 422/140, 422/231, 234, 235; 570/246, 251
See application file for complete search history.

(56) References Cited

U.S. PATENT DOCUMENTS

| | | | | |
|---|---|---|---|---|
| 2,533,058 | A | * | 12/1950 | Shaffer et al. .................. 526/65 |
| 2,775,512 | A | * | 12/1956 | Leithauser et al. ........... 422/200 |
| 3,137,644 | A | * | 6/1964 | Bretschneider .......... 204/157.94 |
| 3,723,545 | A | * | 3/1973 | Nagel et al. .................... 568/855 |
| 4,312,837 | A | * | 1/1982 | Papp et al. ..................... 422/224 |
| 4,347,391 | A | | 8/1982 | Campbell |
| 4,502,992 | A | * | 3/1985 | Hofmann et al. ............. 554/129 |
| 4,613,709 | A | | 9/1986 | Franklin |
| 4,672,142 | A | | 6/1987 | Hundeck et al. |
| 4,740,644 | A | | 4/1988 | Eichhorn et al. |
| 4,783,564 | A | | 11/1988 | Piotrowski et al. |
| 4,873,384 | A | | 10/1989 | Wachi et al. |
| 4,910,354 | A | | 3/1990 | Derleth et al. |

(Continued)

FOREIGN PATENT DOCUMENTS

DE     1 905 517     8/1970

(Continued)

OTHER PUBLICATIONS

DE1905517 Derwent abstract.*

(Continued)

*Primary Examiner* — Jennifer A Leung
(74) *Attorney, Agent, or Firm* — Oblon, Spivak, McClelland, Maier & Neustadt, L.L.P.

(57) ABSTRACT

A reactor for reacting at least two gases in the presence of a liquid phase, provided with an external liquid phase circulation device and including at least one injector for injecting the gases and the externally circulated liquid phase. In the injector the mixing of the gases together and with the externally circulated liquid phase only begins at the outlet of the injector.

20 Claims, 2 Drawing Sheets

U.S. PATENT DOCUMENTS

Figure 1:
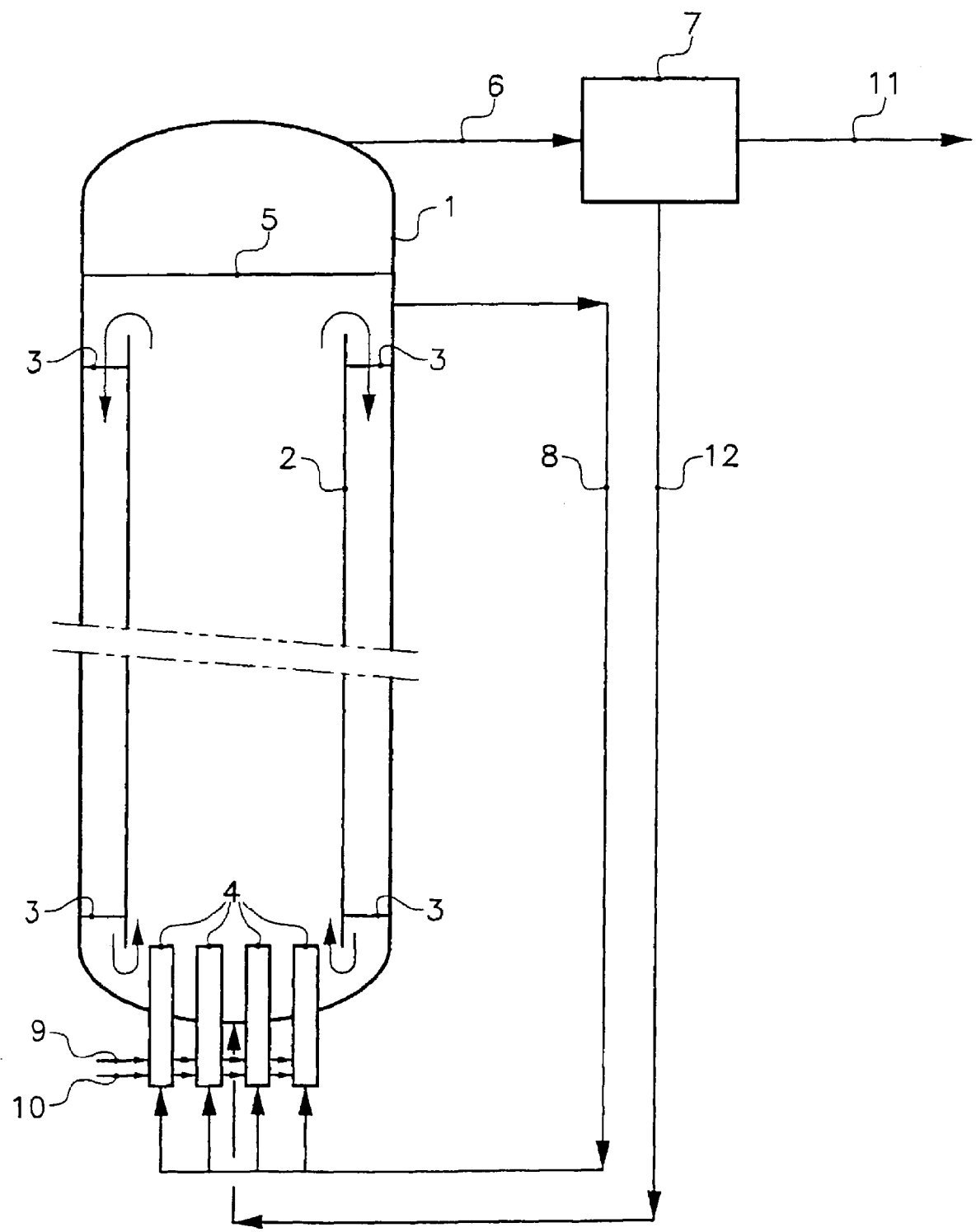

| | | | |
|---|---|---|---|
| 5,120,442 A * | 6/1992 | Kull et al. | 210/621 |
| 5,260,247 A | 11/1993 | Helmut et al. | |
| 5,315,051 A | 5/1994 | Derleth et al. | |
| 5,527,754 A | 6/1996 | Derleth et al. | |
| 6,204,419 B1 | 3/2001 | Eichler et al. | |
| 6,235,953 B1 | 5/2001 | Schwarzmaier et al. | |
| 6,659,636 B1 | 12/2003 | Matula | |
| 6,736,960 B1 | 5/2004 | Chen et al. | |
| 6,803,342 B1 | 10/2004 | Derleth et al. | |

FOREIGN PATENT DOCUMENTS

| | | | |
|---|---|---|---|
| DE | 1905517 | * | 8/1970 |
| DE | 3 146 246 | | 5/1983 |
| DE | 40 39 960 | | 9/1991 |
| DE | 40 29 314 | | 3/1992 |
| DE | 41 33 810 | | 4/1993 |
| DE | 101 46 778 | | 4/2003 |
| EP | 0 130 499 | | 1/1985 |
| EP | 1 136 443 | | 9/2001 |
| FR | 2 771 655 | | 6/1999 |
| JP | 2000279795 A | * | 10/2000 |
| RU | 2 036 716 | | 6/1995 |
| RU | 2 075 344 | | 3/1997 |
| RU | 2 106 907 | | 3/1998 |
| SU | 1 766 486 | | 10/1992 |
| WO | 02 20443 | | 3/2002 |

OTHER PUBLICATIONS

U.S. Appl. No. 11/914,048, filed Nov. 9, 2007, Strebelle, et al.
U.S. Appl. No. 06/854,695, filed Apr. 22, 1986.
U.S. Appl. No. 08/350,976, filed Nov. 29, 1994.
U.S. Appl. No. 60/539,583, filed Jan. 29, 2004, Strebelle.
U.S. Appl. No. 10/567,263, filed Feb. 6, 2006, Strebelle.
U.S. Appl. No. 10/579,094, filed May 12, 2006, Strebelle et al.
U.S. Appl. No. 11/815,505, filed Aug. 3, 2007, Strebelle et al.
Derwent abstract for DE 1905517 A, published Jan. 27, 1977.

* cited by examiner

REACTOR AND METHOD FOR REACTING AT LEAST TWO GASES IN THE PRESENCE OF A LIQUID PHASE

The present invention relates to a reactor for reacting at least two gases in the presence of a liquid phase, and to a method using this reactor. It relates more particularly to a reactor and to a method for producing 1,2-dichloroethane (DCE) by direct chlorination of ethylene.

In reactions between gases that take place in the presence of a liquid phase, the quality of mixing of the gases in the liquid phase is critical for obtaining a high conversion rate and selectivity. This includes the reaction for producing DCE by direct chlorination of ethylene and the reaction for producing 1,1,2-trichloroethane (T112) by direct chlorination of vinyl chloride.

In the particular case of the reaction for producing DCE by direct chlorination of ethylene, the liquid phase comprises DCE and the gases used (chlorine and ethylene) are generally fed to the reactor in a prior mixture with liquid DCE that is taken from the reactor, externally circulated, and returned to the reactor.

Thus, patent application DE 4039960 describes a method and a reactor for the direct chlorination of ethylene, in which the chlorine and ethylene are fed to the reactor via a single injector that also mixes them, prior to feeding them to the reactor, in a part of the externally circulated DCE. Such a system is not optimal in terms of the quality of mixing of the gases in the liquid phase, an important parameter for obtaining a high conversion rate and selectivity, and is also not optimal in terms of safety.

It is accordingly the object of the present invention to provide a reactor (and a method using the same) for reacting at least two gases in the presence of a liquid phase, allowing a significant improvement in the quality of mixing of the gases in the liquid phase and hence an improvement in the conversion rate and selectivity, and which also enhances the safety of the method, particularly in the case of highly reactive gases.

For this purpose, the present invention relates to a reactor for reacting at least two gases in the presence of a liquid phase, comprising a closed chamber provided with an external liquid phase circulation device and comprising at least one injector for injecting the gases and the externally circulated liquid phase, the said injector being such that the mixing of the gases together and with the externally circulated liquid phase only begins at the injector outlet.

Reactor according to the present invention means a closed chamber containing a liquid phase in which (generally chemical) reactions can take place, and which is provided with devices for feeding reactant gases thereto, for removing the reaction product or products therefrom, and for circulating at least part of the liquid phase internally and/or externally.

According to the invention, the reactor comprises at least one injector. Depending on the size of the reactor, it may be advantageous to have more than one injector, preferably at least 2, and in a particularly preferred manner at least 3; this makes it possible, inter alia, to shut off one or more of the injectors under low reactor operating conditions, thereby maintaining a sufficient speed of the gases, even under low conditions, to ensure proper mixing. The maximum number of injectors will be set by the geometric size limitations of the circuits and by the cost of building the equipment. Advantageously, the maximum number of injectors is no more than 8, preferably it is no more than 5. It is particularly preferable for the reactor according to the invention to comprise 4 injectors.

To ensure the best possible homogenization of the gases in the liquid phase, in the case of a plurality of gases, the injectors are generally uniformly distributed in the bottom of the reactor and/or on its side. Preferably, the injector or injectors are located in the bottom of the reactor.

The term injector used in the singular below is intended to mean both the singular and the plural.

The injector used in the reactor according to the invention is a device for both optimizing the mixing of the gases together and with the liquid phase, and for circulating a part of the liquid phase. It is such that the mixing of the gases together and with the externally circulated liquid phase only begins at the outlet of the injector; thus, the reaction between the gases only takes place in the reactor itself, where it is easier to control.

For this purpose, according to a preferred embodiment of the present invention, the injector comprises at least three nozzles for separately injecting the externally circulated liquid phase and the gases.

The injector nozzles may be of any shape. They are preferably concentric.

Thus, according to a particularly preferred embodiment of the present invention, the injector comprises at least three concentric nozzles, that is, at least one central nozzle and at least two respectively intermediate and outer nozzles each comprising a side opening.

According to a very particularly preferred embodiment of the present invention, the injector comprises at least three concentric nozzles, that is, at least one central nozzle for feeding the externally circulated liquid phase and at least two respectively intermediate and outer nozzles each comprising a side opening for feeding a gas.

The size of these nozzles (and their cross section in particular) is suitable for the flow rates of liquid and gas to be provided. Thus, the outer nozzle advantageously has a diameter greater than or equal to 200 mm, preferably greater than or equal to 250 mm. The outer nozzle advantageously has a diameter lower than or equal to 500 mm, preferably lower than or equal to 400 mm. The central nozzle (that is, the one through which the part of externally circulated liquid phase enters the injector) advantageously has a diameter of between 40 and 60%, preferably equal to 50% of the diameter of the outer nozzle. The intermediate nozzle advantageously has a diameter of between 70 and 90%, preferably equal to 80% of the diameter of the outer nozzle.

As to the side gas feed openings, they are generally substantially cylindrical with a cross section at least equal to the cross section of the corresponding nozzle in its widest portion.

In a particularly advantageous manner, the gas feed nozzles have a restriction of their useful cross section at the outlet of the injectors. This restriction of useful cross section (available for the flow of the gas) increases the speed of the gases at this point, where they flow into the reactor and where their flow mixes with the flow of externally circulated liquid phase, thereby making the said mixing more effective and facilitating its uniform incorporation with the liquid phase present in the reactor, optionally in internal circulation. In the particular cases of the direct chlorination of ethylene and the direct chlorination of vinyl chloride, as regards the ethylene or vinyl chloride feed nozzle, this restriction of useful cross section is advantageously such that the speed of the ethylene or of the vinyl chloride is between 10 and 50 m/s, preferably between 12 and 36 m/s, in a particularly preferred manner it is equal to 24 n/s. As to the chlorine feed nozzle, this restriction of useful cross section is advantageously such that the speed of the chlorine is between 15 and 45 m/s, preferably equal to 30 m/s.

The restriction of useful cross section can be achieved by any appropriate means. Preferably, it is achieved by progressive narrowing of the tube diameter.

The reactor according to the invention may be of any shape, in particular substantially spherical or cylindrical, cylindrical reactors being the most common. The liquid phase can be circulated externally using any device known for this purpose, for example by means of a pump. However, the external liquid phase circulation device is advantageously based on the mechanism of natural circulation.

For the purposes of the present intervention, natural circulation means the spontaneous movement induced by the difference in density of the phases. This difference may have various causes, for example the thermosiphon effect or the introduction of a gas into the liquid phase.

The reactor according to the invention generally comprises pressure, temperature, flow control devices, etc., and may also comprise one or more stirring devices (mechanical or other). Advantageously, the reactor comprises a device for internally circulating the liquid phase. For this purpose, the reactor preferably comprises one or more internal walls (that is, plates of any shape and orientation fully located inside the chamber) that favour the homogenization of the reaction liquid phase due to various mechanisms: turbulence, thermosiphon effect. In a particularly preferred manner, the reactor according to the invention, at least along a portion of its height, comprises an internal wall substantially parallel to the chamber and into which the injector discharges. This wall thereby serves to exploit the mechanism of natural circulation.

Advantageously, the injector is accordingly fixed so that its outlet end reaches higher than the bottommost portion of the internal wall, level with this wall or lower than it. Preferably, it is fixed so that this end reaches level with the bottommost portion of the internal wall or lower than it. In a particularly preferred manner, it is fixed so that this end reaches level with the bottommost portion of the internal wall.

When the reactor is cylindrical, the diameter of the internal space bounded by the internal wall is advantageously at least equal to 50% of the reactor diameter. When the reactor is cylindrical, the diameter of the internal space bounded by the internal wall is advantageously no more than 90% of the reactor diameter. Preferably, the diameter of the internal space bounded by the internal wall is equal to 70% of the reactor diameter.

When the reactor is cylindrical, the distance between the bottommost portion of the internal wall and the bottom of the reactor in its bottommost portion is advantageously at least equal to 15% and no more than 30% of the reactor diameter.

It may be advantageous to have a reactor comprising at least two injectors. In fact, such a reactor has the advantage of allowing easier adjustment during changes in operating conditions, particularly the advantage of being more effective under low operating conditions, for example by shutting off one or more injectors under low reactor operating conditions, and thereby of maintaining a sufficient speed of the gases to ensure proper mixing, even under lower operating conditions.

This is why, according to a preferred variant, the present invention relates to a reactor (1) for reacting at least two gases in the presence of a liquid phase, comprising a closed chamber provided with an external liquid phase circulation device (8) and comprising at least two injectors (4) for each injecting the gases (9) (10) and the externally circulated liquid phase (8).

The injectors used are devices for both optimizing the mixing of the gases together and with the liquid phase and for circulating a part of the liquid phase. These injectors can either cause the mixing of the gases together within the injector, or begin this mixing at their outlet. The latter alternative is preferred for safety reasons in the case of highly reactive gases because, thereby, their reaction only takes place in the reactor itself, where it is easily controlled. In a particularly advantageous manner, the gas mixture only enters into contact with the liquid phase and is only mixed with it after issuing from the injectors. The injectors advantageously have the characteristics defined previously.

The reactor according to the invention can be used in numerous technical fields involving methods in which at least one step consists of a reaction between at least two gases in the presence of a liquid phase. The present invention accordingly also relates to a method for reacting at least two gases in the presence of a liquid phase and using a reactor as described above. It relates more particularly to a method in which the reaction product is liquid or boiling at the reaction temperature, and in which it at least partly constitutes the liquid phase in which the reaction takes place. In this case, the external circulation of the liquid phase essentially serves to ensure the presence of a sufficient quantity of liquid phase in the reactor, because the reaction product is generally withdrawn continuously from the reactor. Two particular cases of such a method are the direct chlorination of ethylene, that is, the reaction between chlorine and ethylene to form DCE, and the direct chlorination of vinyl chloride, that is, the reaction between chlorine and vinyl chloride to form T112. In the first preferred case, the gases are chlorine and ethylene and the liquid phase comprises DCE. In the second preferred case, the gases are chlorine and vinyl chloride and the liquid phase comprises T112.

For the purposes of the present invention, ethylene means pure ethylene but also any mixture containing a significant quantity thereof. The same applies to chlorine and vinyl chloride. The vinyl chloride may in particular be vinyl chloride recovered after polymerization.

There are essentially two technologies for producing DCE or T112 to which the method according to the invention can apply: those called boiling technologies (under a pressure and a temperature such that the liquid phase boils) and those called subcooling technologies (at a temperature kept below the boiling point of the liquid phase corresponding to the operating pressure). Boiling technologies have yielded good results particularly for the production of DCE. They have the advantage of yielding pure DCE, since it is produced from vapours generated by the boiling of DCE, which are simply condensed by any known device. They also have the advantage of allowing recovery of the heat of reaction at a useful level. In the case of subcooling technologies, on the contrary, since DCE or T112 are obtained by withdrawal from the liquid phase, they contain the catalyst that must be removed, and this is generally done by a series of steps that reduce the economics of the method.

Examples of known catalysts for the chlorination of ethylene and vinyl chloride include $FeCl_3$ and its complexes with other alkaline chlorides, particularly lithium tetrachloroferrate (as described in patent application NL 6901398).

When the method according to the invention is used with subcooling technologies, it has yielded good results when operating at a temperature higher than or equal to 50° C., preferably higher than or equal to 60° C. but lower than or equal to 80° C., preferably lower than or equal to 70° C. and with a gas phase pressure higher than or equal to 0.5, preferably higher than or equal to 1 bar absolute, but lower than or equal to 10, preferably lower than or equal to 3 bar absolute.

In the method according to the invention, the reaction advantageously takes place according to the boiling chlorination technology, in which natural circulation can be exploited for the external circulation of the liquid phase to the reactor. In particular, the method according to the invention has yielded good results when operating at a temperature higher than or equal to 60° C., preferably to 90° C., in a particularly preferred manner to 95° C., but advantageously lower than or equal to 150° C., preferably to 135° C. and with a gas phase pressure advantageously higher than or equal to 0.2, preferably to 0.5, in a particularly preferred manner to 1.2, in a very particularly preferred manner to 1.5 bar absolute, but advantageously lower than or equal to 10, preferably to 6 bar absolute.

In the particular case in which the gases are fed at the bottom of the reactor, it is particularly advantageous for their pressure (and hence their speed) to be sufficient to overcome the liquid head, the pressure drops and any overpressure present in the gas phase above the liquid phase in the reactor. The gas pressure at the injector outlet is advantageously at least 0.1, preferably at least 0.2 bar higher than the gas phase pressure above the liquid phase in the reactor and advantageously no more than 1.2, preferably no more than 0.8 bar higher than the gas phase pressure above the liquid phase in the reactor. As to the inlet pressures, for a given injector design, they are variable according to the desired outlet pressure and concentrations. Thus, in the case of chlorine, ethylene and vinyl chloride, these are advantageously fed to the injectors at pressures of 0.1 to 10, preferably of 0.1 to 3 bar higher than the injector outlet pressure.

In a particularly advantageous manner, in the case of boiling technologies applied to the production of DCE, the operation takes place at a temperature of 95 to 135° C., with an absolute gas phase pressure of 1.5 to 6 bar, and by feeding the chlorine and ethylene at pressures suitable for obtaining a pressure of 1.7 to 6.8 bar at the injector outlet.

In a particularly advantageous manner, in the case of boiling technologies applied to the production of T112, the operation takes place at a temperature of 95 to 135° C., with an absolute gas phase pressure of 0.2 to 6 bar, and by feeding the chlorine and vinyl chloride at pressures suitable for obtaining a pressure of 0.4 to 6.8 bar at the injector outlet.

In a particularly preferred manner, the method according to the invention is the direct chlorination of ethylene.

The reactor and the method according to the present invention are illustrated in a non-limiting manner by the FIG. 1 (overall view of such a reactor) and 2 (diagram of one of the injectors present in this reactor).

FIG. 1 shows a reactor consisting essentially of a substantially cylindrical outer chamber (1) and comprising a cylindrical internal wall (2) held by supports (3). Thanks to the presence of this cylindrical wall (2), the reaction liquid phase (DCE) is internally circulated by the mechanism of natural circulation (see the arrows for the liquid movement). A series (four) of injectors (4) terminate at the interior of this wall, level with the bottommost portion thereof. The liquid phase that rises up to the level (5) is boiling and the DCE vapours are withdrawn therefrom via the pipe (6) that conveys them to a condensation system (7) where they are converted to liquid DCE (reaction product) that is partly returned to the reactor via the pipe (12) and partly removed via the pipe (11). The external circulation pipe (8) overflows to supply the bottom portion of the injectors (4), which are also laterally fed with ethylene and chlorine respectively via the pipes (9) and (10). These injectors hence feed the reactor both with reactant gases (ethylene and chlorine) and with externally circulated liquid phase (DCE). They avoid the mixing of chlorine and ethylene in the absence of a liquid phase.

Figure 2:
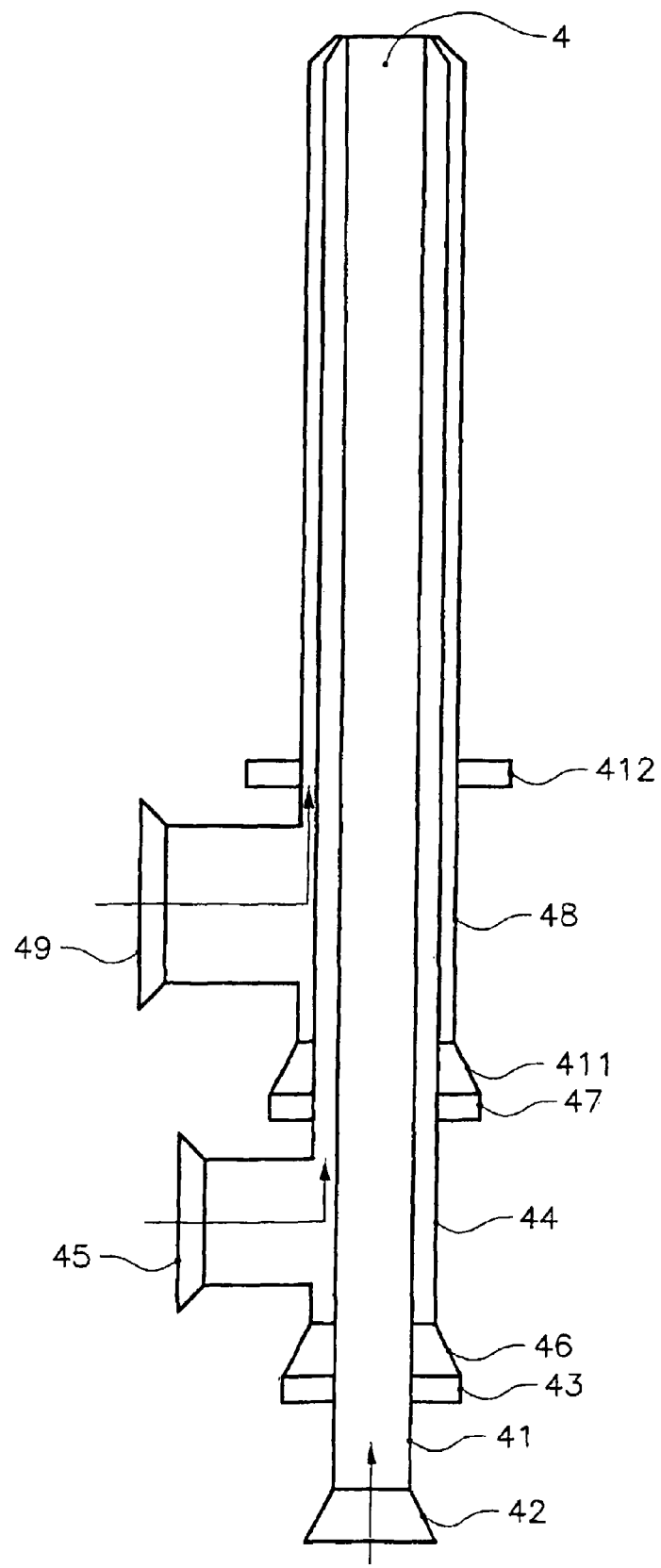

FIG. 2 schematically shows one of the injectors (4) that are provided with a central nozzle (41) to feed externally circulated liquid phase via the pipe (8) (not shown in this figure), the said central nozzle (41) comprising a fitting (42) for the pipe (8) and a fitting (43) for the intermediate chlorine feed nozzle (44). The latter comprises a side opening (45) for feeding chlorine, a fitting (46) for the central nozzle (41) and a fitting (47) for the outer ethylene feed nozzle (48). The latter also comprises a side opening (49) for feeding ethylene, and two fittings: one fitting (411) for the intermediate nozzle (44) and one fitting (412) for the installation of the injector in the chamber (1). The gas feed nozzles (44) and (48) have a restricted cross section at the outlet end of the injector.

The invention claimed is:

1. A reactor for reacting at least two gases in the presence of a liquid phase, comprising:
   a closed chamber including an external liquid phase circulation device and including at least one injector with an injector outlet in the closed chamber,
   wherein each of the at least one injector injects the at least two gases and the externally circulated liquid phase,
   wherein the injector is configured such that mixing of any of the gases together begins only at the injector outlet, and
   wherein mixing of any of the at least two gases with the externally circulated liquid phase only begins at the injector outlet.

2. The reactor according to claim 1, wherein the at least one injector comprises at least three nozzles that separately inject the externally circulated liquid phase and the gases.

3. The reactor according to claim 1, wherein the at least one injector comprises at least three concentric nozzles, including at least one central nozzle and at least two respectively intermediate and outer nozzles, each of the intermediate nozzle and outer nozzle comprising a dedicated side opening.

4. The reactor according to claim 1, wherein the at least one injector comprises at least three concentric nozzles, including at least one central nozzle for feeding the externally circulated liquid phase and at least two respectively intermediate and outer nozzles each comprising a side opening for feeding a gas.

5. The reactor according to claim 4, wherein the intermediate and outer nozzles have a restriction of their useful cross section at the outlet of the at least one injector.

6. The reactor according to claim 1, wherein the external liquid phase circulation device is based on a mechanism of natural circulation.

7. The reactor according to claim 1, further comprising a device that internally circulates the liquid phase.

8. A reactor for reacting at least two gases in the presence of a liquid phase, comprising:
   a closed chamber including an external liquid phase circulation device and including at least two injectors that each injects the at least two gases and the externally circulated liquid phase,
   wherein each of the at least two injectors comprises at least three nozzles that separately inject the externally circulated liquid phase and the at least two gases, respectively, and
   wherein each of the at least three nozzles opens directly into the chamber.

9. A method comprising:
   providing a reactor including a closed chamber with an external liquid phase circulation device and including at least one injector with an injector outlet in the closed chamber, wherein each of the at least one injector injects the at least two gases and the externally circulated liquid phase, wherein the injector is configured such that mixing of any of the gases together begins only at the injector outlet, and wherein mixing of any of the at least two gases with the externally circulated liquid phase only begins at the injector outlet; and reacting the at least two gases in the presence of the liquid phase via the provided reactor.

10. The method according to claim 9, wherein the gases are chlorine and ethylene, and the liquid phase comprises 1,2-dichloroethane (DCE).

11. The method according to claim 9, wherein the gases are chlorine and vinyl chloride, and the liquid phase comprises 1,1,2-trichloroethane (T112).

12. A method comprising:

providing a closed chamber including an external liquid phase circulation device and including at least two injectors that each injects the at least two gases and the externally circulated liquid phase, wherein each of the at least two injectors comprises at least three nozzles that separately inject the externally circulated liquid phase and the at least two gases, respectively, and each of the at least three nozzles opens directly into the chamber; and reacting the at least two gases in the presence of the liquid phase via the provided reactor.

13. The method according to claim 12, wherein the gases are chlorine and ethylene, and the liquid phase comprises 1,2-dichloroethane (DCF).

14. The method according to claim 12, wherein the gases are chlorine and vinyl chloride, and the liquid phase comprises 1,1,2-trichloroethane (T112).

15. A reactor according to claim 1, wherein the at least two gases includes first and second gases, and each of the at least one injector includes a first inlet port coupled to a supply of the first gas, a second inlet port coupled to a supply of the second gas, and a third inlet port coupled to a supply of the liquid phase, wherein the first and second gases are chlorine and ethylene, respectively, and the liquid phase comprises 1,2-dichloroethane.

16. A reactor according to claim 1, wherein the at least two gases includes first and second gases, and each of the at least one injector includes a first inlet port coupled to a supply of the first gas, a second inlet port coupled to a supply of the second gas, and a third inlet port coupled to a supply of the liquid phase, wherein the first and second gases are chlorine and vinyl chloride, respectively, and the liquid phase comprises 1,1,2-trichloroethane.

17. A reactor according to claim 8, wherein the at least two gases includes first and second gases, and each of the at least one injector includes a first inlet port coupled to a supply of the first gas, a second inlet port coupled to a supply of the second gas, and a third inlet port coupled to a supply of the liquid phase, wherein the first and second gases are chlorine and ethylene, respectively, and the liquid phase comprises 1,2-dichloroethane.

18. A reactor according to claim 8, wherein the at least two gases includes first and second gases, and each of the at least one injector includes a first inlet port coupled to a supply of the first gas, a second inlet port coupled to a supply of the second gas, and a third inlet port coupled to a supply of the liquid phase, wherein the first and second gases are chlorine and vinyl chloride, respectively, and the liquid phase comprises 1,1,2-trichloroethane.

19. A reactor according to claim 8, wherein the at least three nozzles are concentric and include at least one central nozzle for feeding the externally circulated liquid phase and at least two respectively intermediate and outer nozzles each comprising a side opening for feeding a gas.

20. A reactor according to claim 19, wherein the intermediate and outer nozzles have a restriction of their useful cross section at the outlet of the at least one injector.

* * * * *

UNITED STATES PATENT AND TRADEMARK OFFICE
CERTIFICATE OF CORRECTION

| | | |
|---|---|---|
| PATENT NO. | : 7,943,099 B2 | Page 1 of 1 |
| APPLICATION NO. | : 11/719652 | |
| DATED | : May 17, 2011 | |
| INVENTOR(S) | : Michel Strebelle et al. | |

It is certified that error appears in the above-identified patent and that said Letters Patent is hereby corrected as shown below:

In column 7, line 31, change "(DCF)" to --(DCE)--.

Signed and Sealed this
Sixteenth Day of August, 2011

David J. Kappos
*Director of the United States Patent and Trademark Office*